US009354192B2

(12) United States Patent
Jiang et al.

(10) Patent No.: US 9,354,192 B2
(45) Date of Patent: May 31, 2016

(54) FERROELECTRIC ANALYZING DEVICE AND METHOD FOR ADJUSTING FERROELECTRIC DOMAIN SWITCHING SPEED

(75) Inventors: Anquan Jiang, Shanghai (CN); Xiaobing Liu, Shanghai (CN)

(73) Assignee: Fudan University, Shanghai (CN)

( * ) Notice: Subject to any disclaimer, the term of this patent is extended or adjusted under 35 U.S.C. 154(b) by 507 days.

(21) Appl. No.: 13/387,044

(22) PCT Filed: Apr. 4, 2011

(86) PCT No.: PCT/CN2011/000578
§ 371 (c)(1),
(2), (4) Date: Nov. 19, 2013

(87) PCT Pub. No.: WO2012/092689
PCT Pub. Date: Jul. 12, 2012

(65) Prior Publication Data
US 2014/0074417 A1    Mar. 13, 2014

(30) Foreign Application Priority Data
Jan. 5, 2011  (CN) .......................... 2011 1 0000987

(51) Int. Cl.
*G01R 19/00*    (2006.01)
*G01R 27/00*    (2006.01)
(Continued)

(52) U.S. Cl.
CPC .......... *G01N 27/041* (2013.01); *G01R 27/2623* (2013.01)

(58) Field of Classification Search
CPC combination set(s) only.
See application file for complete search history.

(56) References Cited

U.S. PATENT DOCUMENTS 6,466,039 B1 * 10/2002 Gruverman .............. 324/754.03
2005/0248973 A1 * 11/2005 Cima et al. ..................... 365/145

FOREIGN PATENT DOCUMENTS

CN    1547036 A  * 11/2004  ............. G01R 27/26
CN    2747587    * 12/2005  ............. G01R 31/00
(Continued)

OTHER PUBLICATIONS

Written opinion of the International Search Authority dated Sep. 21, 2011 in PCT/CN2011/000578.*
(Continued)

*Primary Examiner* — Huan Tran
(74) *Attorney, Agent, or Firm* — McDonnell Boehnen Hulbert & Berghoff LLP

(57) ABSTRACT

The present invention relates to a ferroelectric analyzing device and a method for adjusting ferroelectric domain switching speed with the ferroelectric analyzing device, and pertains to the technical field of characteristic test of solid-state dielectrics. The ferroelectric analyzing device comprises a voltage pulse generator for generating square pulse signal, which is biased on a ferroelectric thin film so as to switch the polarization of ferroelectric domains, the ferroelectric analyzing device further comprises a variable resistor which is connected in series with the ferroelectric thin film. The variable resistor is used for adjusting domain switching current so as to realize adjustment of domain switching speed of ferroelectric domains. In the method, the square pulse signal is biased on the ferroelectric thin film, and an adjustment of domain switching speed of ferroelectric domains can be realized by adjusting the resistance value of the variable resistor. The device can adjust the moving speed of ferroelectric domains continuously, and can also adjust the coercive voltage of the ferroelectric thin film; it does not depend on the voltage pulse signal generator, can be easily adjusted continuously, has a wide range of adjustment, and is reliable in data tests.

15 Claims, 2 Drawing Sheets

(51) Int. Cl.
*G01N 27/04* (2006.01)
*G01R 27/26* (2006.01)

(56) References Cited

FOREIGN PATENT DOCUMENTS

| CN | 101158712 | * | 4/2008 | ............. | G01R 19/00 |
| CN | 101718810 A | * | 6/2010 | ............. | G01R 19/00 |
| CN | 101718810 B | * | 1/2012 | ............. | G01R 19/00 |
| JP | 11195370 | * | 10/1999 | ............. | G01R 31/00 |

OTHER PUBLICATIONS

Zhong Weilie, "The Physics of Ferroelectrics", Science Press, pp. 292-294, 1996.
Xu Yuhuan, "Ferroelectric and Piezoelectric Materials", Science Press, pp. 103-104, 1978.

* cited by examiner

FERROELECTRIC ANALYZING DEVICE AND METHOD FOR ADJUSTING FERROELECTRIC DOMAIN SWITCHING SPEED

FIELD OF THE INVENTION

The present invention pertains to the technical field of a characteristic test of solid-state dielectrics and relates to a ferroelectric analyzing device of ferroelectric thin films, and to a method for adjusting ferroelectric domain switching speed with the ferroelectric analyzing device.

BACKGROUND

The dielectric is characterized in that it transmits, stores or records the action and influence of external bias electric field signal in an electric polarization manner in which the gravity centers of positive and negative charges do not coincide. Therefore, dielectric constant is a most fundamental parameter which characterizes a dielectric. Ferroelectrics are a special kind of dielectric materials which has a large dielectric constant, a strong non-linear effect, a large strength of spontaneous polarization, as well as significant dependencies upon temperature and frequency. In recent years, ferroelectric thin film based material has been widely used in ferroelectric random access memory (FeRAM), dynamic random access memory (DRAM), non-refrigerating infrared detector, thin film dielectric capacitor, electric field modulated microwave device, AC electroluminescent device and thin film sensor, etc.

In a ferroelectric thin film, e.g., in a ferroelectric capacitor formed based on a ferroelectric thin film, when the direction of external bias electric field is different from the direction of electrical domains, if the voltage for generating the external bias electric field is larger than the coercive voltage (Vc) of the ferroelectric thin film, the ferroelectric domains will move, i.e., the ferroelectric domains will switch their polarization direction; the moving speed of ferroelectric domain which reflects the switching speed of polarization is in direct proportion to the switching current. Generally, the external bias electric field is realized by applying a voltage pulse.

The prior art of ferroelectric analyzing apparatus can make tests on various characteristic parameters of ferroelectric thin film, e.g., remaining polarization charges, domain switching speed. When it is required to adjust the domain switching speed of ferroelectric domains, the amplitude of voltage pulse (i.e., the amount of voltage biased on the ferroelectric thin film) is generally changed so as to realize such an adjustment. This is because during the domain switching, the required charge equals to an integration of current flowing through a ferroelectric thin film over time, and the variation of voltage amplitude will result in variation of the current and further lead to variation of time for the required integration charge, thus making it possible to adjust the domain switching speed of ferroelectric domains.

Obviously, with the method for adjusting the domain switching speed of ferroelectric domains of the prior ferroelectric analyzing apparatus, it is required to change the shape of voltage pulse continuously during adjusting, which is a complicated process and has a demanding requirement on the voltage pulse generator of ferroelectric analyzing apparatus; meanwhile, since the range of variation of the voltage pulse is easily limited by apparatus and instruments, it is difficult to realize an adjustment of domain switching speed of ferroelectric domains in a sufficiently wide range of orders.

SUMMARY OF THE INVENTION

One objective of the invention is to propose a ferroelectric analyzing device and method in which adjustment of domain switching speed of ferroelectric domains is made easily.

The other objective of the invention is to make the coercive voltage adjustable simultaneously when the domain switching speed is being adjusted.

The above or other objectives of the invention are realized in the following technical solutions.

According to one aspect of this invention, a ferroelectric analyzing device is provided comprising a voltage pulse generator for generating square voltage pulse signal, which is biased on a ferroelectric thin film so as to switch polarization of ferroelectric domains. The ferroelectric analyzing device further comprises a variable resistor which is connected in series with a ferroelectric thin film. The variable resistor is used for adjusting domain switching current so as to realize adjustment of domain switching speed of ferroelectric domains.

According to an embodiment of the ferroelectric analyzing device provided by the invention, the ferroelectric analyzing device further comprises a signal collecting device for collecting signals across the variable resistor.

Preferably, the signal collecting device is oscilloscope.

Preferably, the collected signals comprise of the square pulse of voltage biased on the variable resistor during domain switching and/or the time of domain switching.

Preferably, the range of resistance value of the variable resistor is substantially from 1 to $10^9 \Omega$.

According to the ferroelectric analyzing device provided by the invention, the domain switching current is calculated by the following relationship:

$$I_{sw}=(V-V_c)/R_t=(V-V_c)/(R_1+R_2)$$

wherein, $I_{sw}$ is the domain switching current, V is the voltage amplitude of the square pulse, $V_c$ is the coercive voltage, $R_t$ is the overall resistance of circuit, $R_2$ is the resistance value of the variable resistor, $R_1$ is the resistor connected in series with $R_2$ and comprising the internal resistor of the voltage pulse generator.

The required charge for domain switching is calculated by the following relationship:

$$Q_{sw}=|\int I_{sw}dt|$$

wherein $I_{sw}$ is the domain switching current, $Q_{sw}$ is the required charge for domain switching.

According to another aspect of the invention, a method for adjusting ferroelectric domain switching speed with the above-described ferroelectric analyzing device is provided, wherein the square pulse signal is biased on the ferroelectric thin film, and the adjustment of ferroelectric domain switching speed is realized by adjusting the resistance value of the variable resistor.

Preferably, before biasing of a square voltage pulse signal, a pre-polarization of ferroelectric domains is realized by biasing a presetting pulse signal on the ferroelectric thin film.

Preferably, the polarity of the presetting pulse signal is opposite to the polarity of the square voltage pulse signal.

According to the method for adjusting ferroelectric domain switching speed provided by the invention, the adjustment of the coercive voltage of the ferroelectric thin film can be realized simultaneously when the resistance value of the variable resistor is adjusted.

According to an embodiment of the method for adjusting ferroelectric domain switching speed provided by the invention, the domain switching current is calculated by the following relationship:

$$I_{sw}=(V-V_c)/R_t=(V-V_c)/(R_1+R_2)$$

wherein, $I_{sw}$ is the domain switching current, V is the voltage amplitude of the square pulse, $V_c$ is the coercive voltage, $R_t$ is the overall resistance of circuit, $R_2$ is the resistance value of the variable resistor, $R_1$ is the resistor connected in series with $R_2$ and comprising the internal resistor of the voltage pulse generator.

The required charge for domain switching is calculated by the following relationship:

$$Q_{sw}=|\int I_{sw}dt|$$

wherein $I_{sw}$ is the domain switching current, $Q_{sw}$ is the required charge for domain switching.

According to another embodiment of the method for adjusting ferroelectric domain switching speed provided by the invention, the ferroelectric analyzing device further comprises a signal collecting device for collecting signals across the variable resistor; the signals collected by the signal collecting device comprises the platform altitude amplitude of voltage biased on the variable resistor during domain switching and/or the time of domain switching.

Preferably, the domain switching current $I_{sw}$ is calculated by dividing the applied voltage on the variable resistor by its resistance value; further, the coercive voltage of the ferroelectric thin film is calculated by the following relationship:

$$I_{sw}=(V-V_c)/R_t=(V-V_c)/(R_1+R_2)$$

wherein, $I_{sw}$ is the domain switching current, V is the voltage amplitude of the square pulse, $V_c$ is the coercive voltage, $R_t$ is the overall resistance of circuit, $R_2$ is the resistance value of the variable resistor, $R_1$ is the resistor connected in series with $R_2$ and comprising the internal resistor of the voltage pulse generator.

The technical effects brought about by the invention are described as follows. By adding the variable resistor, the domain switching current is adjusted so that the moving speed of frontier ferroelectric domains (i.e., the speed of domain switching) is adjusted; moreover, the coercive voltage $V_c$ of the ferroelectric thin film can also be adjusted simultaneously when the resistance value of the variable resistor is adjusted. Therefore, when the ferroelectric analyzing device provided by the invention is adjusting ferroelectric domain switching current, it does not depend on the voltage amplitude of the pulse signal generator, can be easily adjusted continuously, has a wide range of adjustment, and is reliable in data tests.

BRIEF DESCRIPTION OF THE DRAWINGS

The above and other objectives and advantages of this invention will become more apparent from the following detailed description with the reference to accompanying drawings, wherein identical or similar elements are denoted by identical signs.

DETAILED DESCRIPTION OF THE INVENTION

Some of the many possible embodiments of the invention will be described hereinafter in order to provide a basic understanding of the invention which will not set the protection limit on crucial or decisive elements of the invention or the scope of protection. It is easily understood that according to the technical solutions of the invention, those with ordinary skills in the art can propose other alternative implementations without modifying the substantive spirit of the invention. Therefore, the following particular embodiments as well as the drawings are merely illustrative description of the technical solutions of the invention, and should not be considered as the whole invention or as defining or limiting the technical solutions of the invention.

Figure 1:
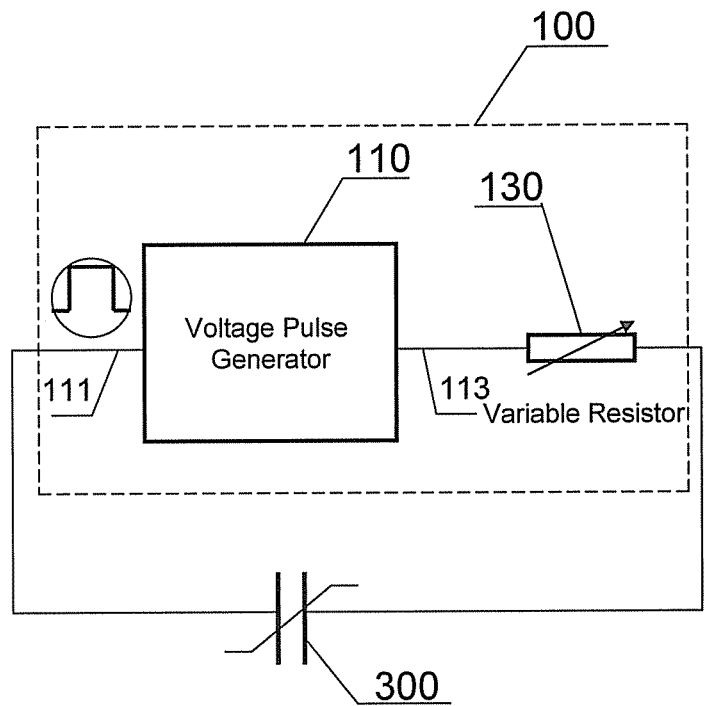
FIG. 1 is a schematic structural view of a ferroelectric analyzing device provided according to an embodiment of the invention.

FIG. 1 shows a schematic view of a ferroelectric analyzing device provided according to an embodiment of the invention, wherein a ferroelectric thin film forms the ferroelectric capacitor 300 shown in FIG. 1, and the ferroelectric analyzing device 100 is used for analyzing and testing the ferroelectric capacitor. In this embodiment, the ferroelectric capacitor 300 can be a sample of a Pt/IrO$_2$/Pb(Zr$_{0.4}$Ti$_{0.6}$)O$_3$(PZT)/IrO$_2$/Pt/Si structure, the thickness of the ferroelectric thin film (Pb(Zr$_{0.4}$Ti$_{0.6}$)O$_3$) is about 140 nm, and the area of top electrode is about $1.0\times10^{-4}$ cm$^2$.

Referring to FIG. 1, the ferroelectric analyzing device 100 mainly comprises a voltage pulse generator 110 and a variable resistor 130 connected in series to the input end or output end of the voltage pulse generator 110 (in this embodiment, 111 is output end, 113 is input end, and the variable resistor 130 is connected in series to the input end). The voltage pulse generator 110 is used for generating a square pulse signal, which, when biased on the ferroelectric capacitor, can switch the polarization of ferroelectric domains for the ferroelectric thin film in the capacitor under the stimulation of an electric field generated by the voltage pulse. The specific shape of the voltage pulse signal is not limited to embodiments of the invention. For example, the parameters of square pulse signal such as voltage amplitude, pulse width and voltage polarity, etc., can be set according to predetermined requirements. Specifically, the voltage pulse generator 110 can use Agilent 81150A arbitrary waveform generator so as to generate predetermined requirements on the pulse shape by setting the Agilent 81150A arbitrary waveform.

Continuing with FIG. 1, the tested ferroelectric capacitor 300 is connected in series between the input end and output end of the voltage pulse generator 110. Therefore, the output voltage pulse signal from the voltage pulse generator 110 can be biased on the ferroelectric thin film of the capacitor 300. In the invention, the variable resistor 130 is also connected in series in the circuit between the ferroelectric capacitor 300 and the voltage pulse generator 110. Thus, the voltage pulse signal is biased on the variable resistor 130 and the ferroelectric capacitor 300 simultaneously, and the variable resistor 130 and the ferroelectric capacitor 300 form a RC circuit. Of course, if an internal resistor R1 exists in the voltage pulse generator 110, the voltage pulse signal is also biased on the internal resistor R1 simultaneously.

Assuming that the initially ferroelectric capacitor 300 has been uniformly polarized with all ferroelectric domains pointing to one direction after a presetting pulse action (e.g., when applied to ferroelectric information storage, ferroelectric capacitor 300 has already been pre-programmed to "0" status or "1" status), the resistance value set by the variable resistor 130 is $R_2$. The square pulse generator 110 outputs a voltage pulse signal (e.g., the voltage amplitude is V, and the pulse width is T). In order to switch polarization of ferroelectric capacitor, the voltage V is greater than the coercive voltage $V_c$ of the ferroelectric thin film and the voltage polarity is opposite to the presetting pulse. During domain switching of the ferroelectric capacitor, the required charge equals to an integration of current flowing through ferroelectric thin film over domain switching time, i.e.:

$$Q_{sw}=|\int I_{sw}dt| \quad (1)$$

wherein $Q_{sw}$ is required charge for domain switching, and $I_{sw}$ is the domain switching current.

In the circuit of shown in FIG. 1, $I_{sw}$ is circuit current, since the voltage on the ferroelectric capacitor equals to the coercive voltage $V_c$ during domain switching time, therefore:

$$I_{sw}=(V-V_c)/R_t=(V-V_c)/(R_1+R_2) \quad (2)$$

wherein $I_{sw}$ is the domain switching current, V is voltage amplitude of the square pulse, $V_c$ is the coercive voltage, $R_t$ is overall resistance of circuit. In this embodiment, $R_t$ is the sum of the variable resistance $R_2$ and the internal resistance $R_1$ of the voltage pulse generator. It is also noted that in other embodiments, when another resistor having a substantially fixed resistance value or an equivalent resistor is also connected in series in the RC circuit, $R_1$ also represents the sum of inner resistance of the voltage pulse generator and the other serially connected resistors.

The polarization charge $2P_rS$ required for ferroelectric domain switching of a ferroelectric thin film is nearly fixed and constant, where $P_r$ is the remanent polarization and S is the electrode area. Therefore, when $I_{sw}$ varies, it can be known from the relationship $2P_rS/I_{sw}$ that the time required for domain switching can vary, i.e., the speed of domain switching can vary.

Therefore, as can be known from the relationship (2) that in the invention, $I_{sw}$ can be adjusted by adjusting the resistance value of the variable resistor 130 (i.e., $R_2$ varies) so that the domain switching speed of ferroelectric domain for ferroelectric capacitor can be adjusted (for the same voltage pulse and the same $R_2$ value, the coercive voltage $V_c$ keeps constant during domain switching). Moreover, since the variable resistor 130 can be adjusted continuously with a certain range of resistance value, the speed of domain switching can also be adjusted continuously, i.e., a continuous adjustment of moving speed of ferroelectric domains is realized. In this embodiment, the range of resistance value of the variable resistor 130 can be from about $1\Omega$ to about $10^9\Omega$.

It is noted that in event that the area S of the ferroelectric capacitor 300 and $Q_{sw}$ are known, $P_{sw}$ can be calculated by the ferroelectric analyzing device according to the following relationship (3):

$$P_{sw}=Q_{sw}/S \quad (3)$$

wherein $P_{sw}$ is domain switching value, S is the area of the ferroelectric capacitor, i.e., the area of the ferroelectric thin film, and $Q_{sw}$ is the required charge for domain switching. When the presetting voltage polarity is the same to the switching pulse voltage, we got the nonswitching polarization $P_{nsw}$, and the difference between $P_{sw}$ and $P_{nsw}$ is $2P_r$.

Figure 2:
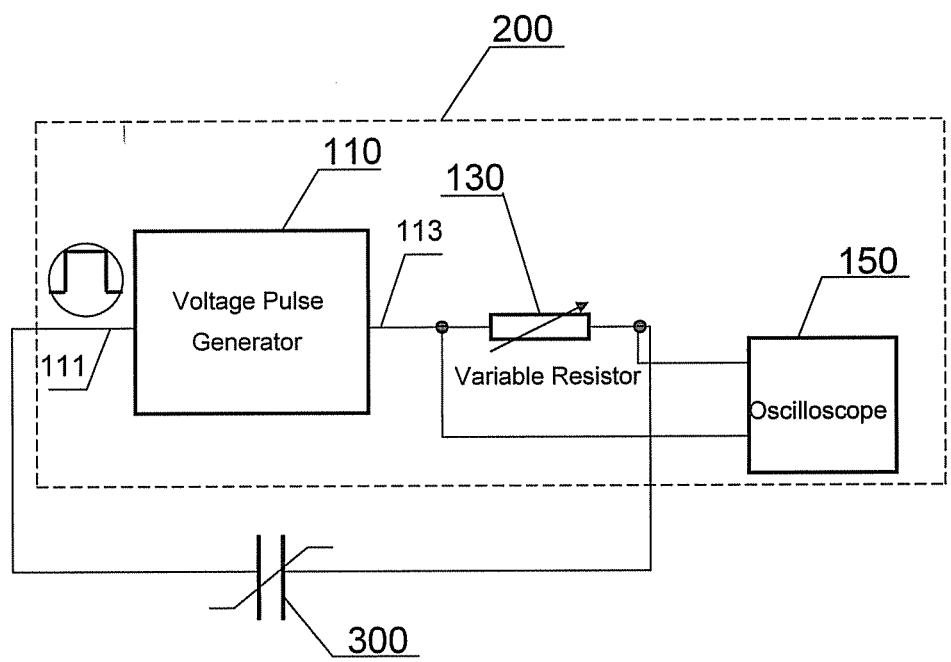
FIG. 2 is another schematic view of an example of the ferroelectric analyzing device shown in FIG. 1 for a particular application.

FIG. 2 shows another schematic view of an example of the ferroelectric analyzing device for a particular application. As compared with the structure shown in FIG. 1, in the ferroelectric analyzing device 200 shown in FIG. 2, a signal collecting device for collecting electrical signals across the variable resistor 130 is added. In this embodiment, the signal collecting device is oscilloscope 150. Meanwhile, $R_1$ in the relationship (2) is still substantially equal to the internal resistance of the voltage pulse generator 110 (since the internal resistance of the oscilloscope 150 is much greater than $R_2$). The oscilloscope 150 is connected to both ends of the variable resistor 130 in parallel so that the voltage across the variable resistor can be recorded during testing, and by identifying a variation of voltage waveform amplitude before and after domain switching, the transient voltage biased on the variable resistor 130 during domain switching can be collected or read out with time (i.e., by further subtracting the voltage biased on the total in-series resistors in the system, we got $V_c$; and by reading out the width of voltage transient over time generated by the applied voltage biased on the variable resistor 130 during movement of ferroelectric domains, the domain switching time or moving time t of electric domains is identified (in some samples of ferroelectric capacitor, the domain switching time t is derived from calculation). Generally, the transient voltage across the resistor 130 is a plateau in an ideal ferroelectric capacitor with a very narrow $V_c$ distribution over the film area. Therefore, $I_{sw}$ in the relationship (2) is derived by dividing the collected voltage platform height by the resistance value thereof ($R_2$), and $Q_{sw}$ can be calculated by making use of the collected domain switching time t and the calculated $I_{sw}$.

It is noted that the specific structure of the signal collecting device is not limited by this embodiment.

Figure 3:
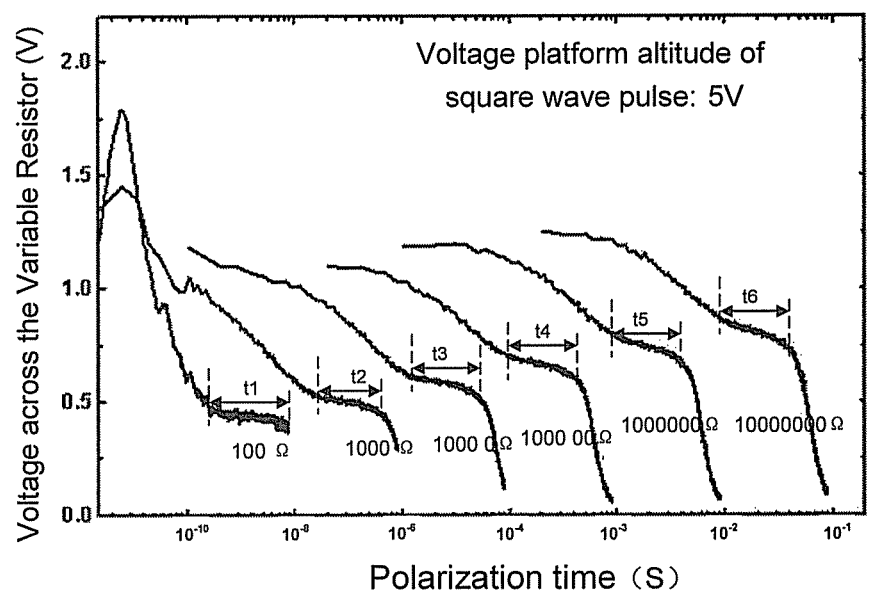
FIG. 3 is a schematic view showing the results of variation of domain switching speed with the variation of resistance value of the variable resistor in the device shown in FIG. 2.

FIG. 3 shows a schematic view showing the results of variation of domain switching speed with the variation of resistance value of the variable resistor in the device shown in FIG. 2. In FIG. 3, many curves are shown when the variable resistor 300 varies from $100\Omega$ to $1,000\Omega$, $10,000\Omega$, $100,000\Omega$, $1,000,000\Omega$ and $10,000,000\Omega$. As can be seen from FIG. 3, each curve has a platform stage in which the sustained time length is the domain switching time. For example, when the variable resistor 300 is adjusted to $1000\Omega$, the voltage across the variable resistor 300 is kept for a time $t_2$ at about 0.5 V in the corresponding curve, i.e., the domain switching time is $t_2$. At this point, the shape of square pulse is fixed and constant, and the resistance value of the variable resistor is constant at $1000\Omega$. Therefore, the coercive voltage $V_c$ is also unchanged; the domain switching current $I_{sw}$ can be substantially derived by dividing the voltage (0.5V) across the variable resistor 130 by the resistance value ($1000\Omega$) of the variable resistor 300; and the corresponding $V_c$ at this point can be further calculated by the relationship (2).

When the variable resistor 300 is in other situations, the corresponding domain switching current $I_{sw}$ and $V_c$ can also be calculated. Therefore, not only can it be seen from the drawings that the domain switching speed is lowered with the increase of the variable resistor 130, but also it can be found that $V_c$ varies therewith. Therefore, it can be known that by adjusting the resistance value of the variable resistor, not only the domain switching speed can be adjusted, but also the coercive voltage $V_c$ of the ferroelectric thin film can be adjusted. Moreover, since the adjustment range of resistance can be set large (e.g., across 9 orders of magnitude), which is unlike the amplitude modulation of square pulses whose voltage range is easily limited by pulse generator (it is not suitable for the amplitude of pulse to be overly large), the domain switching speed can be adjusted within a greater range. The measurement range of the ferroelectric analyzing device is extremely large and the test of data is highly reliable.

It is known from the above that the ferroelectric analyzing device of the invention can realize a continuous adjustment of the domain switching speed of ferroelectric domains. That is, by adjusting the resistance value of the variable resistor, the domain switching speed of ferroelectric domains can be adjusted, and simultaneously, the coercive voltage $V_c$ of the ferroelectric thin film can be adjusted. The specific process of this adjusting method will be described as follows.

Firstly, as shown in FIG. 2, the voltage pulse generator 110 generates a presetting pulse so that a presetting ferroelectric domains with the uniform polarization are formed in the ferroelectric capacitor 300 (i.e., to realize a pre-polarization of the ferroelectric domains), wherein the voltage amplitude of the presetting pulse can be the same as the voltage amplitude of the square pulse applied for domain switching, but with an opposite polarity; moreover, the width of the preset pulse is wide enough to sufficiently switch all ferroelectric domains. For example, the voltage of the presetting voltage pulse is −5V, and the pulse width is 100 milliseconds.

Then, the voltage pulse generator 110 generates a square pulse signal for domain switching of ferroelectric domains. Specifically, the voltage of the square pulse signal can be 5 V; the pulse width can be 5 milliseconds. When this square pulse signal is biased on the ferroelectric capacitor 300, a continuous adjustment of domain switching speed can be realized by adjusting the resistance value of the variable resistor, and an adjustment of the coercive voltage $V_c$ can be realized simultaneously. Therefore, an adjustment of domain switching speed can be conveniently realized without varying the square pulse signal. In a particular application, the resistance value $R_2$ of the variable resistor can be adjusted to an appropriate value so as to obtain a predetermined required domain switching speed value. The structure is simple, and it is easy to make the adjustment.

By adjusting the domain switching speed of ferroelectric domains using the ferroelectric analyzing device of this invention, a high practical application merit is obtained. Taking the application where the ferroelectric thin film is used in a ferroelectric memory of 1T1C structure as example, through the above tests, the domain switching current $I_{sw}$, the domain switching time t and the coercive voltage $V_c$ of the ferroelectric capacitor (C) can be obtained when the overall resistance $R_t$ of circuit is set at a certain value. Therefore, when performing an writing operation on the memory, if the overall resistance of programming circuit is set to be equal to $R_t$, the writing current is set to be greater than or equal to the domain switching current $I_{sw}$, the writing time is set to be greater than or equal to the domain switching time t, and writing voltage is set to be greater than or equal to the coercive voltage $V_c$, the writing operation can be made safely. Moreover, the overall resistance of circuit (i.e., the variable capacitor) can be adjusted according to requirements on writing voltage and current, etc. (e.g., the limitations on voltage pulse amplitude and magnitude of current) so that when biased by a specific square pulse waveform output from the programming device, an writing operation on the memory can be easily realized.

It is noted that the application range of the ferroelectric thin film is not limited to the above situations. The specific practical application merits of adjusting domain switching speed of ferroelectric domains using the ferroelectric analyzing device of the invention will not be described in detail herein.

Those skilled in the art should understand that the ferroelectric analyzing device provided in the above embodiments may further comprise other functional components that are commonly known by those skilled in the art and will not be described in detail herein.

The above embodiments mainly describe the ferroelectric analyzing device of the invention and the method for adjusting ferroelectric domain switching speed with the ferroelectric analyzing device. While some of the embodiments of the invention have been described, those skilled in the art will understand that the invention can be implemented in many other forms without departing from its spirit and scope. Therefore, the illustrated examples and embodiments should be considered as schematic rather than being limiting. The invention can cover various modifications and substitutes without departing from the spirit and scope of the invention defined by appended claims.

The invention claimed is:

1. A ferroelectric analyzing device comprising a voltage pulse generator for generating square pulse signal, which is biased on a ferroelectric thin film so as to switch polarization of ferroelectric domains, characterized in that the ferroelectric analyzing device further comprises a variable resistor which is connected in series with the ferroelectric thin film wherein the variable resistor is used for adjusting domain switching current so as to realize adjustment of domain switching speed of ferroelectric domains.

2. The ferroelectric analyzing device according to claim 1, characterized in that the ferroelectric analyzing device further comprises a signal collecting device for collecting signals across the variable resistor.

3. The ferroelectric analyzing device according to claim 2, characterized in that the signal collecting device is oscilloscope.

4. The ferroelectric analyzing device according to claim 2, characterized in that the collected signals comprise the platform amplitude of voltage biased on the variable resistor during domain switching and/or the time of domain switching.

5. The ferroelectric analyzing device according to claim 1, characterized in that the range of resistance value of the variable resistor is substantially from 1Ω to $10^9$Ω.

6. The ferroelectric analyzing device according to claim 1, characterized in that the domain switching current is calculated by the following relationship:

$$I_{sw}=(V-V_c)/R_t=(V-V_c)/(R_1+R_2)$$

wherein, $I_{sw}$ is the domain switching current, V is the voltage amplitude of the square pulse, $V_c$ is the coercive voltage, $R_t$ is the overall resistance of circuit, $R_2$ is the resistance value of the variable resistor, $R_1$ is the resistor connected in series with $R_2$ and comprises the internal resistor of the voltage pulse generator.

7. The ferroelectric analyzing device according to claim 6, characterized in that the required charge for domain switching is calculated by the following relationship:

$$Q_{sw}=|\int I_{sw}dt|$$

wherein $I_{sw}$ is the domain switching current, $Q_{sw}$ is the required charge for domain switching.

8. A method for adjusting ferroelectric domain switching speed with the ferroelectric analyzing device according to claim 1, the method including the steps of:
biasing the square pulse signal on the ferroelectric thin film; and
adjusting the ferroelectric domain switching speed by adjusting the resistance value of the variable resistor.

9. The method for adjusting ferroelectric domain switching speed according to claim 8, characterized in that before biasing the square pulse signal, realizing a pre-polarization of ferroelectric domain by biasing a presetting pulse signal on the ferroelectric thin film.

10. The method for adjusting ferroelectric domain switching speed according to claim 9, characterized in that the polarity of the presetting pulse signal is opposite to the polarity of the square pulse signal.

11. The method for adjusting ferroelectric domain switching speed according to claim 8, including adjusting the coercive voltage of the ferroelectric thin film simultaneously with adjusting the resistance value of the variable resistor.

12. The method for adjusting ferroelectric domain switching speed according to claim 8, characterized in that the domain switching current is calculated by the following relationship:

$$I_{sw}=(V-V_c)/R_t=(V-V_c)/(R_1+R_2)$$

wherein, $I_{sw}$ is the domain switching current, V is the voltage amplitude of the square pulse signal, $V_c$ is the coercive voltage, $R_t$ is the overall resistance of circuit, $R_2$ is the resistance value of the variable resistor, $R_1$ is the resistor connected in series with $R_2$ and comprising the internal resistor of the voltage pulse generator.

13. The method for adjusting ferroelectric domain switching speed according to claim 12, characterized in that the required charge for domain switching is calculated by the following relationship:

$$Q_{sw}=|\int I_{sw}dt|$$

wherein $I_{sw}$ is the domain switching current, $Q_{sw}$ is the required charge for domain switching.

14. The method for adjusting ferroelectric domain switching speed according to claim 8, characterized in that the ferroelectric analyzing device further comprises a signal collecting device for collecting signals across the variable resistor; the signals collected by the signal collecting device comprises the platform amplitude of voltage biased on the variable resistor during domain switching and/or the time of domain switching.

15. The method for adjusting ferroelectric domain switching speed according to claim 14, including calculating the domain switching current $I_{sw}$ by dividing the platform amplitude of voltage across the variable resistor by the resistance value of the variable resistor; further, the coercive voltage of the ferroelectric thin film is calculated by the following relationship:

$$I_{sw}=(V-V_c)/R_t=(V-V_c)/(R_1+R_2)$$

wherein $I_{sw}$ is the domain switching current, V is the voltage amplitude of the square pulse signal, and $V_c$ is the coercive voltage, $R_t$ is the overall resistance of circuit, $R_2$ is the resistance value of the variable resistor, $R_1$ is the resistor connected in series with $R_2$ and comprising the inner resistor of the voltage pulse generator.

* * * * *